US012582663B2

(12) United States Patent
Thomas

(10) Patent No.: US 12,582,663 B2
(45) Date of Patent: Mar. 24, 2026

(54) COMPOSITIONS COMPRISING DECARBOXYLATED CANNABINOIDS

(71) Applicant: Natural Extraction Systems, LLC, Boulder, CO (US)

(72) Inventor: C. Russell Thomas, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 975 days.

(21) Appl. No.: 17/638,379

(22) PCT Filed: Aug. 26, 2020

(86) PCT No.: PCT/US2020/048043

§ 371 (c)(1),
(2) Date: Feb. 25, 2022

(87) PCT Pub. No.: WO2021/014572

PCT Pub. Date: Mar. 4, 2021

(65) Prior Publication Data

US 2022/0280444 A1 Sep. 8, 2022

Related U.S. Application Data

(60) Provisional application No. 62/942,443, filed on Dec. 2, 2019, provisional application No. 62/892,178, filed on Aug. 27, 2019.

(51) Int. Cl.

| | |
|---|---|
| *A61K 31/00* | (2006.01) |
| *A23L 33/105* | (2016.01) |
| *A23L 33/13* | (2016.01) |
| *A23L 33/17* | (2016.01) |
| *A61K 9/20* | (2006.01) |
| *A61K 9/48* | (2006.01) |
| *A61K 31/01* | (2006.01) |
| *A61K 31/05* | (2006.01) |
| *A61K 31/353* | (2006.01) |
| *A61K 31/51* | (2006.01) |
| *A61K 31/519* | (2006.01) |
| *A61K 31/7088* | (2006.01) |
| *A61K 33/06* | (2006.01) |
| *A61K 33/26* | (2006.01) |
| *A61K 38/45* | (2006.01) |
| *A61K 47/22* | (2006.01) |

(52) U.S. Cl.
CPC .......... *A61K 31/658* (2023.05); *A23L 33/105* (2016.08); *A23L 33/13* (2016.08); *A23L 33/17* (2016.08); *A61K 9/2054* (2013.01); *A61K 9/4866* (2013.01); *A61K 31/353* (2013.01); *A61K 38/45* (2013.01); *A61K 47/22* (2013.01); *C12Y 205/01102* (2015.07); *A23V 2002/00* (2013.01)

(58) Field of Classification Search
None
See application file for complete search history.

(56) References Cited

U.S. PATENT DOCUMENTS

| | | | | |
|---|---|---|---|---|
| 9,611,460 B2 * | 4/2017 | Page | ....................... | C12P 17/06 |
| 10,195,159 B2 | 2/2019 | Whittle et al. | | |

FOREIGN PATENT DOCUMENTS

WO WO-2019003163 A2 * 1/2019 ............. A61K 31/01

* cited by examiner

*Primary Examiner* — Manjunath N Rao
*Assistant Examiner* — Jae W Lee
(74) *Attorney, Agent, or Firm* — Douglas G. Metcalf

(57) ABSTRACT

Various aspects of this disclosure relate to compositions comprising (i) one or more decarboxylated cannabinoids and (ii) either (a) cellulose I, (b) nucleic acids that comprise one or more nucleotide sequences that encode a geranyl-pyrophosphate-olivetolic acid geranyltransferase, (c) protein that comprises one or more amino acid sequences that encode a geranyl-pyrophosphate-olivetolic acid geranyltransferase, (d) two of a, b, and c, or (e) each of a, b, and c.

15 Claims, No Drawings

COMPOSITIONS COMPRISING DECARBOXYLATED CANNABINOIDS

CROSS-REFERENCE TO RELATED APPLICATIONS

This patent application is the U.S. National Stage under 35 U.S.C. § 371 of International Application No. PCT/US20/48043, which claims priority to U.S. Provisional Patent Application No. 62/892,178, filed Aug. 27, 2019, and U.S. Provisional Patent Application No. 62/942,443, filed Dec. 2, 2019, each of which is incorporated by reference in its entirety.

BACKGROUND

Industrial hemp and other forms of *cannabis* biosynthetically produce cannabinoid carboxylic acids that bind the human cannabinoid receptors with relatively low affinity. The production of industrial hemp extracts, therapeutic pharmaceuticals, and psychoactive drugs from *cannabis* therefore generally utilizes a decarboxylation step, which typically involves prolonged heating. This heating generally results in thermal degradation products and other undesirable chemical modifications. Improved methods to decarboxylate cannabinoids remain desirable.

SUMMARY

Various aspects of this disclosure relate to novel compositions comprising (i) one or more decarboxylated cannabinoids and (ii) another component such as cellulose I. These compositions can be produced as a byproduct using the improved methods to decarboxylate cannabinoids described in U.S. Pat. No. 10,669,248. The byproducts contain, for example, about 0.5 percent to about 5 percent fully-activated cannabinoids as well as vitamins, minerals, protein, and dietary fiber. The byproducts can be formulated into dietary supplements for people, pets, and livestock.

DETAILED DESCRIPTION

Various aspects of this patent document relate to a composition, comprising decarboxylated cannabinoids and nucleic acids, wherein: the decarboxylated cannabinoids comprise one or more of cannabidiol, cannabidivarin, tetrahydrocannabinol, tetrahydrocannabivarin, and cannabigerol; the composition comprises the decarboxylated cannabinoids at a combined concentration of least 0.5 percent and no greater than 5 percent by weight; the composition lacks cannabidiolic acid, cannabidivarin acid, tetrahydrocannabinolic acid, tetrahydrocannabivarin acid, and cannabigerolic acid at a combined concentration greater than 1 percent by weight; and the nucleic acids comprise one or more nucleotide sequences that encode a geranyl-pyrophosphate-olivetolic acid geranyltransferase. In some embodiments, the composition comprises cellulose I. The biosynthesis of cellulose results in cellulose I, which is metastable, and cellulose I irreversibly converts to other forms of cellulose that are commonly used in commercial applications. The presence of cellulose I in a composition indicates that the composition is derived from a plant material that has not undergone a process that denatures cellulose I such as solvent extraction.

"Comprising" and "comprise(s)" refer to open-ended sets such that a composition comprising decarboxylated cannabinoids and nucleic acids can also comprise cellulose I.

"Cannabidiol" refers to 2-[(1R,6R)-6-isopropenyl-3-methylcyclohex-2-en-1-yl]-5-pentylbenzene-1,3-diol. "Cannabidivarin" refers to 2-[(1R,6R)-6-isopropenyl-3-methylcyclohex-2-en-1-yl]-5-propylbenzene-1,3-diol. "Tetrahydrocannabinol" refers to (6aR,10aR)-6,6,9-trimethyl-3-pentyl-6a,7,8,10a-tetrahydro-6H-benzo[c]chromen-1-ol. "Tetrahydrocannabivarin" refers to (6aR,10aR)-6,6,9-trimethyl-3-propyl-6a,7,8,10a-tetrahydro-6H-benzo[c]chromen-1-ol. "Cannabigerol" refers to 2-[(2E)-3,7-dimethylocta-2,6-dienyl]-5-pentyl-benzene-1,3-diol. "Cannabidiolic acid" refers to both 2,4-dihydroxy-3-[(1R,6R)-6-isopropenyl-3-methylcyclohex-2-en-1-yl]-6-pentyl-benzoic acid and its corresponding carboxylate. "Cannabidivarin acid" refers to both 2,4-dihydroxy-3-[(1R,6R)-6-isopropenyl-3-methylcyclohex-2-en-1-yl]-6-propylbenzoic acid and its corresponding carboxylate. "Tetrahydrocannabinolic acid" refers to both (6aR,10aR)-1-hydroxy-6,6,9-trimethyl-3-pentyl-6a,7,8,10a-tetrahydro-6H-benzo[c]chromene-2-carboxylic acid and its corresponding carboxylate. "Tetrahydrocannabivarin acid" refers to both (6aR,10aR)-1-hydroxy-6,6,9-trimethyl-3-propyl-6a,7,8,10a-tetrahydro-6H-benzo[c]chromene-2-carboxylic acid and its corresponding carboxylate. "Cannabigerolic acid" refers to both 2,4-dihydroxy-3-[(2E)-3,7-dimethylocta-2,6-dienyl]-6-pentyl-benzoic acid and its corresponding carboxylate. "Geranyl-pyrophosphate-olivetolic acid geranyltransferase" refers to any protein that is capable of synthesizing cannabigerolic acid (or its conjugate base cannabigerolate) from both olivetolic acid (or its conjugate base olivetolate) and geranyl pyrophosphate such that a cell that synthesizes cannabigerolic acid (or cannabigerolate) from both olivetolic acid (or olivetolate) and geranyl pyrophosphate comprises both (i) protein that comprises one or more amino acid sequences that encode a geranyl-pyrophosphate-olivetolic acid geranyltransferase and (ii) nucleic acids that comprise one or more nucleotide sequences that encode a geranyl-pyrophosphate-olivetolic acid geranyltransferase. GenBank accession numbers for putative geranyl-pyrophosphate-olivetolic acid geranyltransferases are catalogued, for example, in Luo, NATURE, 567:123-126 (2019).

Various aspects of this patent document relate to a composition, comprising decarboxylated cannabinoids and protein, wherein: the decarboxylated cannabinoids comprise one or more of cannabidiol, cannabidivarin, tetrahydrocannabinol, tetrahydrocannabivarin, and cannabigerol; the composition comprises the decarboxylated cannabinoids at a combined concentration of at least 0.5 percent and no greater than 5 percent by weight; the composition lacks cannabidiolic acid, cannabidivarin acid, tetrahydrocannabinolic acid, tetrahydrocannabivarin acid, and cannabigerolic acid at a combined concentration greater than 1 percent by weight; and the protein comprises one or more amino acid sequences that encode a geranyl-pyrophosphate-olivetolic acid geranyltransferase. In some embodiments, the composition comprises cellulose I.

Various aspects of this patent document relate to a composition, comprising cellulose I and decarboxylated cannabinoids, wherein: the decarboxylated cannabinoids comprise one or more of cannabidiol, cannabidivarin, tetrahydrocannabinol, tetrahydrocannabivarin, and cannabigerol; the composition comprises the decarboxylated cannabinoids at a combined concentration of at least 0.5 percent and no greater than 5 percent by weight; and the composition lacks cannabidiolic acid, cannabidivarin acid, tetrahydrocannabinolic acid, tetrahydrocannabivarin acid, and cannabigerolic acid at a combined concentration greater than 1 percent by weight.

In some embodiments, the composition comprises nucleic acids. In some specific embodiments, the nucleic acids comprise one or more nucleotide sequences that encode a geranyl-pyrophosphate-olivetolic acid geranyltransferase.

In some embodiments, the composition comprises protein. In some specific embodiments, the protein comprises one or more amino acid sequences that encode a geranyl-pyrophosphate-olivetolic acid geranyltransferase.

In preferred embodiments, the decarboxylated cannabinoids consist of one or more of cannabidiol, cannabidivarin, tetrahydrocannabinol, tetrahydrocannabivarin, and cannabigerol. "Consist(s) of" and "consisting of" refer to closed sets such that decarboxylated cannabinoids that consist of one or more of cannabidiol, cannabidivarin, tetrahydrocannabinol, tetrahydrocannabivarin, and cannabigerol cannot comprise any other cannabinoid. A composition that comprises decarboxylated cannabinoids that consist of one or more of cannabidiol, cannabidivarin, tetrahydrocannabinol, tetrahydrocannabivarin, and cannabigerol may nevertheless comprise other cannabinoids such as cannabinol, but "consist of" indicates that the "decarboxylated cannabinoids" do not comprise any other cannabinoid that is present in the composition.

In some embodiments, the composition comprises the decarboxylated cannabinoids at a combined concentration of at least 0.8 percent and no greater than 4 percent by weight.

In some embodiments, the composition comprises chlorophyll. In some specific embodiments, the composition comprises chlorophyll a. In some specific embodiments, the composition comprises chlorophyll b. In some very specific embodiments, the composition comprises chlorophyll a and chlorophyll b.

In some embodiments, the cellulose I comprises cellulose Ialpha and cellulose Ibeta. In some embodiments, the cellulose I is present in microfibrils. In some specific embodiments, the cellulose I comprises cellulose Ialpha and cellulose Ibeta, and the cellulose Ialpha and the cellulose Ibeta are present in microfibrils.

In some embodiments, the composition comprises cellulose I at a concentration of at least 5 percent and no greater than 50 percent by weight. In some specific embodiments, the composition comprises cellulose I at a concentration of either at least 5 percent and no greater than 25 percent by weight; at least 15 percent and no greater than 35 percent by weight; at least 25 percent and no greater than 45 percent by weight; or at least 35 percent and no greater than 45 percent by weight.

In some embodiments, the composition comprises hemicellulose. In some embodiments, the composition comprises pectin. In some specific embodiments, the composition comprises hemicellulose and pectin.

In some embodiments, the composition comprises calcium (for example, as Ca++). In some embodiments, the composition comprises iron (for example, as Fe+++). In some embodiments, the composition comprises magnesium (for example, as Mg++). In some embodiments, the composition comprises manganese (for example, as Mn++). In some embodiments, the composition comprises zinc (for example, as Zn++). In some embodiments, the composition comprises phosphorous (for example, as hydrogen phosphate). In some embodiments, the composition comprises vitamin B6 (for example, as pyridoxal). In some embodiments, the composition comprises folate. In some embodiments, the composition comprises thiamin. In some embodiments, the composition comprises riboflavin. In some specific embodiments, the composition comprises two, three, four, five, six, seven, eight, nine, or each of calcium, iron, magnesium, manganese, zinc, phosphorous, vitamin B6, folate, thiamin, and riboflavin.

In some embodiments, the composition has a surface-area-to-volume ratio greater than 100 per meter. In some specific embodiments, the composition has a surface-area-to-volume ratio greater than 500 per meter. In some very specific embodiments, the composition has a surface-area-to-volume ratio greater than 1000 per meter.

In some embodiments, the composition comprises cannabidiol at a concentration of at least 0.05 percent by weight. In some specific embodiments, the composition comprises cannabidiol at a concentration of at least 0.08 percent and no greater than 4 percent by weight. In some specific embodiments, the composition comprises cannabidiol at a concentration of at least 0.5 percent and no greater than 5 percent by weight. In some very specific embodiments, the composition comprises cannabidiol at a concentration of at least 0.05 percent and no greater than 1 percent by weight. In some very specific embodiments, the composition comprises cannabidiol at a concentration of at least 0.5 percent and no greater than 1.5 percent by weight. In some very specific embodiments, the composition comprises cannabidiol at a concentration of at least 0.75 percent and no greater than 2.5 percent by weight.

In some embodiments, the composition comprises cannabidiol and any cannabidiolic acid that is present in the composition at a ratio of at least 5:1 by weight (for example, at least 5 grams of cannabidiol for every gram of cannabidiolic acid). In some specific embodiments, the composition comprises cannabidiol and any cannabidiolic acid that is present in the composition at a ratio of at least 10:1 by weight.

In some embodiments, the composition comprises tetrahydrocannabinol at a concentration of at least 0.05 percent by weight. In some specific embodiments, the composition comprises tetrahydrocannabinol at a concentration of at least 0.08 percent and no greater than 4 percent by weight. In some specific embodiments, the composition comprises tetrahydrocannabinol at a concentration of at least 0.5 percent and no greater than 5 percent by weight. In some very specific embodiments, the composition comprises tetrahydrocannabinol at a concentration of at least 0.05 percent and no greater than 1 percent by weight. In some very specific embodiments, the composition comprises tetrahydrocannabinol at a concentration of at least 0.5 percent and no greater than 1.5 percent by weight. In some very specific embodiments, the composition comprises tetrahydrocannabinol at a concentration of at least 0.75 percent and no greater than 2.5 percent by weight.

In some embodiments, the composition comprises tetrahydrocannabinol and any tetrahydrocannabinolic acid that is present in the composition at a ratio of at least 5:1 by weight. In some specific embodiments, the composition comprises tetrahydrocannabinol and any tetrahydrocannabinolic acid that is present in the composition at a ratio of at least 10:1 by weight.

In some embodiments, the composition comprises cannabigerol at a concentration of at least 0.05 percent by weight. In some specific embodiments, the composition comprises cannabigerol at a concentration of at least 0.08 percent and no greater than 4 percent by weight. In some specific embodiments, the composition comprises cannabigerol at a concentration of at least 0.5 percent and no greater than 5 percent by weight. In some very specific embodiments, the composition comprises cannabigerol at a concentration of at least 0.05 percent and no greater than 1 percent by weight. In some very specific embodiments, the composition comprises cannabigerol at a concentration of at least 0.5 percent and no greater than 1.5 percent by weight. In some very specific embodiments, the composition comprises cannabigerol at a concentration of at least 0.75 percent and no greater than 2.5 percent by weight.

In some embodiments, the composition comprises cannabigerol and any cannabigerolic acid that is present in the composition at a ratio of at least 5:1 by weight. In some specific embodiments, the composition comprises cannabigerol and any cannabigerolic acid that is present in the composition at a ratio of at least 10:1 by weight.

In some embodiments, the composition comprises cannabidivarin at a concentration of at least 0.05 percent by weight. In some specific embodiments, the composition comprises cannabidivarin at a concentration of at least 0.08 percent and no greater than 4 percent by weight. In some specific embodiments, the composition comprises cannabidivarin at a concentration of at least 0.5 percent and no greater than 5 percent by weight. In some very specific embodiments, the composition comprises cannabidivarin at a concentration of at least 0.05 percent and no greater than 1 percent by weight. In some very specific embodiments, the composition comprises cannabidivarin at a concentration of at least 0.5 percent and no greater than 1.5 percent by weight. In some very specific embodiments, the composition comprises cannabidivarin at a concentration of at least 0.75 percent and no greater than 2.5 percent by weight.

In some embodiments, the composition comprises cannabidivarin and any cannabidivarin acid that is present in the composition at a ratio of at least 5:1 by weight. In some specific embodiments, the composition comprises cannabidivarin and any cannabidivarin acid that is present in the composition at a ratio of at least 10:1 by weight.

In some embodiments, the composition comprises tetrahydrocannabivarin at a concentration of at least 0.05 percent by weight. In some specific embodiments, the composition comprises tetrahydrocannabivarin at a concentration of at least 0.08 percent and no greater than 4 percent by weight. In some specific embodiments, the composition comprises tetrahydrocannabivarin at a concentration of at least 0.5 percent and no greater than 5 percent by weight. In some very specific embodiments, the composition comprises tetrahydrocannabivarin at a concentration of at least 0.05 percent and no greater than 1 percent by weight. In some very specific embodiments, the composition comprises tetrahydrocannabivarin at a concentration of at least 0.5 percent and no greater than 1.5 percent by weight. In some very specific embodiments, the composition comprises tetrahydrocannabivarin at a concentration of at least 0.75 percent and no greater than 2.5 percent by weight.

In some embodiments, the composition comprises tetrahydrocannabivarin and any tetrahydrocannabivarin acid that is present in the composition at a ratio of at least 5:1 by weight. In some specific embodiments, the composition comprises tetrahydrocannabivarin and any tetrahydrocannabivarin acid that is present in the composition at a ratio of at least 10:1 by weight.

In some embodiments, the composition comprises cannabichromene at a concentration of at least 0.05 percent by weight. In some specific embodiments, the composition comprises cannabichromene at a concentration of at least 0.08 percent and no greater than 4 percent by weight. In some specific embodiments, the composition comprises cannabichromene at a concentration of at least 0.5 percent and no greater than 5 percent by weight. In some very specific embodiments, the composition comprises cannabichromene at a concentration of at least 0.05 percent and no greater than 1 percent by weight. In some very specific embodiments, the composition comprises cannabichromene at a concentration of at least 0.5 percent and no greater than 1.5 percent by weight. In some very specific embodiments, the composition comprises cannabichromene at a concentration of at least 0.75 percent and no greater than 2.5 percent by weight. "Cannabichromene" refers to 2-methyl-2-(4-methylpent-3-enyl)-7-pentylchromen-5-ol without reference to any specific stereochemistry.

In some embodiments, the composition comprises cannabichromene and any cannabichromenic acid that is present in the composition at a ratio of at least 5:1 by weight. In some specific embodiments, the composition comprises cannabichromene and any cannabichromenic acid that is present in the composition at a ratio of at least 10:1 by weight. "Cannabichromenic acid" refers to both 5-hydroxy-2-methyl-2-(4-methylpent-3-enyl)-7-pentyl-chromene-6-carboxylic acid and its corresponding carboxylate without reference to any specific stereochemistry.

In some embodiments, the composition comprises (6aS, 10aR)-tetrahydrocannabinol or (6aS,10aR)-tetrahydrocannabivarin. In some specific embodiments, the composition comprises one or both of (6aS,10aR)-tetrahydrocannabinol and (6aS,10aR)-tetrahydrocannabivarin at a combined concentration of at least 0.05 percent and no greater than 5 percent by weight. In some very specific embodiments, the composition comprises (6aS,10aR)-tetrahydrocannabinol at a concentration of at least 0.05 percent by weight. In some very specific embodiments, the composition comprises (6aS, 10aR)-tetrahydrocannabivarin at a concentration of at least 0.05 percent by weight. "(6aS,10aR)-tetrahydrocannabinol" refers to (6aS,10aR)-6,6,9-trimethyl-3-pentyl-6a,7,8,10a-tetrahydro-6H-benzo[c]chromen-1-ol. "(6aS,10aR)-tetrahydrocannabivarin" refers to (6aS,10 aR)-6,6,9-trimethyl-3-propyl-6a,7,8,10a-tetrahydro-6H-benzo[c]chromen-1-ol.

In some embodiments, the composition comprises one or more of caryophyllene oxide, humulene epoxide I, humulene epoxide II, humulene epoxide III, bicyclohumuladiol, tricyclohumuladiol, tricyclohumuladiol II, humulenol, and a stereoisomer of any of the foregoing. In some specific embodiments, the composition comprises either caryophyllene oxide or a stereoisomer of caryophyllene oxide at a concentration of at least 0.1 and no greater than 1000 parts per million by weight. In some specific embodiments, the composition comprises either humulene epoxide I or a stereoisomer of humulene epoxide I at a concentration of at least 0.1 and no greater than 1000 parts per million by weight. In some specific embodiments, the composition comprises either humulene epoxide II or a stereoisomer of humulene epoxide II at a concentration of at least 0.1 and no greater than 1000 parts per million by weight. In some specific embodiments, the composition comprises either humulene epoxide III or a stereoisomer of humulene epoxide III at a concentration of at least 0.1 and no greater than 1000 parts per million by weight. In some specific embodiments, the composition comprises either bicyclohumuladiol or a stereoisomer of bicyclohumuladiol at a concentration of at least 0.1 and no greater than 1000 parts per million by weight. In some specific embodiments, the composition comprises either tricyclohumuladiol or a stereoisomer of tricyclohumuladiol at a concentration of at least 0.1 and no greater than 1000 parts per million by weight. In some specific embodiments, the composition comprises either tricyclohumuladiol II or a stereoisomer of tricyclohumuladiol II at a concentration of at least 0.1 and no greater than 1000 parts per million by weight. In some specific embodiments, the composition comprises either humulenol or a stereoisomer of humulenol at a concentration of at least 0.1 and no greater than 1000 parts per million by weight. The terms "caryophyllene oxide," "humulene epoxide I," "humulene epoxide II," "humulene epoxide III," "bicyclohumuladiol," "tricyclohumuladiol," "tricyclohumuladiol II," and "humulenol" are defined in PCT Patent Application Publication No. WO 2020/123383 A1, which is incorporated by reference to identify the chemical formulas and structures of the chemical species of this patent document.

In some embodiments, the composition comprises cannabidiol, tetrahydrocannabinol, and cannabigerol at a combined concentration of at least 0.08 percent and no greater than 4 percent by weight. In some embodiments, the composition lacks cannabidiolic acid, tetrahydrocannabinolic acid, and cannabigerolic acid at a combined concentration of greater than 0.1 percent by weight. In some specific embodiments, the composition comprises cannabidiol, tetrahydrocannabinol, and cannabigerol at a combined concentration of at least 0.8 percent and no greater than 4 percent by weight; and the composition lacks cannabidiolic acid, tetrahydrocannabinolic acid, and cannabigerolic acid at a combined concentration of greater than 0.1 percent by weight.

In some embodiments, the composition lacks cannabidiolic acid, cannabidivarin acid, tetrahydrocannabinolic acid, tetrahydrocannabivarin acid, and cannabigerolic acid at a combined concentration greater than 0.1 percent by weight. In some specific embodiments, the composition lacks cannabidiolic acid, cannabidivarin acid, tetrahydrocannabinolic acid, tetrahydrocannabivarin acid, and cannabigerolic acid at a combined concentration greater than 0.05 percent by weight. In some very specific embodiments, the composition lacks cannabidiolic acid, cannabidivarin acid, tetrahydrocannabinolic acid, tetrahydrocannabivarin acid, and cannabigerolic acid at a combined concentration greater than 0.01 percent by weight.

In some embodiments, the composition lacks cannabinol at a concentration greater than 0.1 percent by weight. In some specific embodiments, the composition lacks cannabinol at a concentration greater than 0.05 percent by weight. In some very specific embodiments, the composition lacks cannabinol at a concentration greater than 0.01 percent by weight. "Cannabinol" refers to 6,6,9-trimethyl-3-pentyl-6H-benzo[c]chromen-1-ol.

In some embodiments, the composition lacks delta-8-tetrahydrocannabinol at a concentration greater than 0.1 percent by weight. In some specific embodiments, the composition lacks delta-8-tetrahydrocannabinol at a concentration greater than 0.05 percent by weight. In some very specific embodiments, the composition lacks delta-8-tetrahydrocannabinol at a concentration greater than 0.01 percent by weight. "Delta-8-tetrahydrocannabinol" refers to (6aR,10aR)-6,6,9-trimethyl-3-pentyl-6a,7,10,10a-tetrahydro-6H-benzo[c]chromen-1-ol.

In some embodiments, the composition lacks water at a concentration greater than 5 percent by weight.

In some embodiments, the composition lacks ethanol, isopropanol, propylene glycol, propane, butane, pentane, hexanes, and heptane at a combined concentration greater than 1 percent by weight. In some specific embodiments, the composition lacks ethanol, isopropanol, propylene glycol, propane, butane, pentane, hexanes, and heptane at a combined concentration greater than 0.1 percent by weight.

In some embodiments, the composition lacks molecules that have a boiling point of less than 190 degrees Celsius at atmospheric pressure at a combined concentration greater than 10 percent by weight.

In some embodiments, the composition lacks triglycerides at a concentration greater than 50 percent by weight. In some specific embodiments, the composition lacks triglycerides at a concentration greater than 25 percent by weight.

Various aspects of this patent document relate to a capsule that contains a composition described anywhere in this patent document, wherein the capsule contains at least 5 and no greater than 50 milligrams of one or more of the decarboxylated cannabinoids. In some specific embodiments, the capsule contains at least 5 and no greater than 50 milligrams of cannabidiol. In some specific embodiments, the capsule contains at least 5 and no greater than 50 milligrams of cannabidivarin. In some specific embodiments, the capsule contains at least 5 and no greater than 50 milligrams of tetrahydrocannabinol. In some specific embodiments, the capsule contains at least 5 and no greater than 50 milligrams of tetrahydrocannabivarin. In some specific embodiments, the capsule contains at least 5 and no greater than 50 milligrams of cannabigerol. In some embodiments, the capsule contains at least 100 milligrams and no greater than 4 grams of the composition. In some specific embodiments, the capsule is formulated for oral administration to a human or animal.

Various aspects of this patent document relate to a tablet, consisting of a composition described anywhere in this patent document, wherein the tablet comprises at least 5 and no greater than 50 milligrams of one or more of the decarboxylated cannabinoids. In some embodiments, the tablet comprises at least 5 and no greater than 50 milligrams of cannabidiol. In some embodiments, the tablet comprises at least 5 and no greater than 50 milligrams of cannabidivarin. In some embodiments, the tablet comprises at least 5 and no greater than 50 milligrams of tetrahydrocannabinol. In some embodiments, the tablet comprises at least 5 and no greater than 50 milligrams of tetrahydrocannabivarin. In some embodiments, the tablet comprises at least 5 and no greater than 50 milligrams of cannabigerol. In some embodiments, the tablet consists of at least 100 milligrams and no greater than 4 grams of the composition. In some specific embodiments, the tablet is formulated for oral administration to a human or animal.

Exemplification. Examples 1-3 set forth specific, commercially-relevant embodiments of this disclosure, and examples 1-3 do not limit the scope of the disclosure or any claim that matures from this patent document.

Example 1. Production of Extracted Industrial Hemp

The methods of U.S. Pat. No. 10,669,248 were used to extract industrial hemp. The extracted industrial hemp byproduct was analyzed by an ISO/IEC 17025 accredited third-party cannabinoid testing laboratory to measure cannabinoid concentrations, and various test results are reported in Table 1.

Example 2. Preparation of Herbal Supplement Capsules from Extracted Industrial Hemp The extracted industrial hemp was combined with excipients and additional herbal supplements, and the combination was used to fill capsules that each contain 10, 20, or 40 milligrams of cannabidiol.

Example 3. Preparation of Herbal Supplement Tablets from Extracted Industrial Hemp The extracted industrial hemp is combined with a binder and a diluent and pressed into one-gram tablets that each contain 10 milligrams of cannabidiol.

TABLE 1

Measured Cannabinoid Concentrations by Weight in Processed Hemp

| Sample | CBD | CBDA | THC | THCA | CBG | CBGA | CBC | CBN |
|--------|-----|------|-----|------|-----|------|-----|-----|
| 1 | 0.69% | 0.00% | 0.00% | 0.00% | 0.00% | 0.00% | 0.08% | 0.00% |
| 2 | 0.86% | 0.00% | 0.02% | 0.00% | 0.00% | 0.00% | 0.06% | 0.00% |
| 3 | 0.87% | 0.00% | 0.00% | 0.00% | 0.00% | 0.00% | 0.00% | 0.00% |
| 4 | 1.23% | 0.00% | 0.03% | 0.00% | 0.00% | 0.00% | 0.13% | 0.00% |
| 5 | 1.29% | 0.00% | 0.00% | 0.00% | 0.00% | 0.00% | 0.11% | 0.00% |
| 6 | 1.35% | 0.00% | 0.00% | 0.00% | 0.05% | 0.00% | 0.09% | 0.00% |
| 7 | 1.41% | 0.00% | 0.04% | 0.00% | 0.04% | 0.00% | 0.08% | 0.00% |
| 8 | 1.49% | 0.00% | 0.00% | 0.00% | 0.00% | 0.00% | 0.06% | 0.00% |
| 9 | 1.59% | 0.00% | 0.04% | 0.00% | 0.04% | 0.00% | 0.08% | 0.00% |
| 10 | 1.62% | 0.00% | 0.00% | 0.00% | 0.00% | 0.00% | 0.00% | 0.00% |
| 11 | 1.70% | 0.00% | 0.00% | 0.00% | 0.04% | 0.00% | 0.07% | 0.00% |
| 12 | 2.02% | 0.00% | 0.02% | 0.00% | 0.00% | 0.00% | 0.00% | 0.00% |
| 13 | 2.06% | 0.00% | 0.05% | 0.00% | 0.08% | 0.00% | 0.14% | 0.00% |
| 14 | 2.10% | 0.00% | 0.02% | 0.00% | 0.00% | 0.00% | 0.00% | 0.00% |
| 15 | 2.26% | 0.00% | 0.02% | 0.00% | 0.00% | 0.00% | 0.00% | 0.00% |
| 16 | 2.38% | 0.00% | 0.03% | 0.00% | 0.00% | 0.00% | 0.00% | 0.00% |
| 17 | 2.45% | 0.00% | 0.05% | 0.00% | 0.08% | 0.00% | 0.18% | 0.00% |
| 18 | 2.47% | 0.00% | 0.07% | 0.00% | 0.00% | 0.00% | 0.10% | 0.00% |
| 19 | 2.50% | 0.00% | 0.03% | 0.00% | 0.00% | 0.00% | 0.00% | 0.00% |
| 20 | 2.61% | 0.00% | 0.08% | 0.00% | 0.13% | 0.00% | 0.11% | 0.00% |
| 21 | 2.63% | 0.00% | 0.08% | 0.00% | 0.16% | 0.00% | 0.09% | 0.00% |
| 22 | 2.72% | 0.00% | 0.04% | 0.00% | 0.00% | 0.00% | 0.00% | 0.00% |
| 23 | 3.97% | 0.00% | 0.00% | 0.00% | 0.00% | 0.00% | 0.00% | 0.00% |

What is claimed is:

1. A capsule or tablet composition comprising:

cellulose I;

decarboxylated cannabinoids; and nucleic acids encoding a geranyl-pyrophosphate-olivetolic acid geranyltransferase and/or a geranyl-pyrophosphate-olivetolic acid geranyltransferase protein; wherein:

the capsule or tablet comprises at least 5 and no greater than 50 milligrams of one or more of the decarboxylated cannabinoids;

the decarboxylated cannabinoids comprise one or more of cannabidiol, cannabidivarin, tetrahydrocannabinol, tetrahydrocannabivarin, and cannabigerol;

the composition comprises the decarboxylated cannabinoids at a combined concentration of at least 0.5 percent and no greater than 5 percent by weight; and the composition lacks cannabidiolic acid, cannabidivarin acid, tetrahydrocannabinolic acid, tetrahydrocannabivarin acid, and cannabigerolic acid at a combined concentration greater than 1 percent by weight;

wherein said composition further comprises:

either *bicyclohumuladiol* or a stereoisomer of *bicyclohumuladiol* at a concentration of at least 0.1 and no greater than 1000 parts per million by weight;

either *tricyclohumuladiol* or a stereoisomer of *tricyclohumuladiol* at a concentration of at least 0.1 and no greater than 1000 parts per million by weight; and/or either *tricyclohumuladiol II* or a stereoisomer of *tricyclohumuladiol II* at a concentration of at least 0.1 and no greater than 1000 parts per million by weight (italicized for added emphasis).

2. The composition of claim 1, comprising cannabidiol at a concentration of at least 0.5 percent and no greater than 5 percent by weight.

3. The composition of claim 1, comprising cannabidiol and any cannabidiolic acid that is present in the composition at a ratio of at least 5:1 by weight.

4. The composition of claim 1, comprising tetrahydrocannabinol at a concentration of at least 0.05 percent by weight.

5. The composition of claim 1, comprising tetrahydrocannabinol and any tetrahydrocannabinolic acid that is present in the composition at a ratio of at least 5:1 by weight.

6. The composition of claim 1, comprising cannabigerol at a concentration of at least 0.05 percent by weight.

7. The composition of claim 1, comprising cannabigerol and any cannabigerolic acid that is present in the composition at a ratio of at least 5:1 by weight.

8. The composition of claim 1, comprising cannabidivarin at a concentration of at least 0.05 percent by weight.

9. The composition of claim 1, comprising tetrahydrocannabivarin at a concentration of at least 0.05 percent by weight.

10. The composition of claim 1, comprising tetrahydrocannabivarin and any tetrahydrocannabivarin acid that is present in the composition at a ratio of at least 5:1 by weight.

11. The composition of claim 1, comprising either caryophyllene oxide or a stereoisomer of caryophyllene oxide at a concentration of at least 0.1 and no greater than 1000 parts per million by weight.

12. The composition of claim 1, comprising either humulene epoxide I or a stereoisomer of humulene epoxide I at a concentration of at least 0.1 and no greater than 1000 parts per million by weight.

13. The composition of claim 1, comprising either humulene epoxide II or a stereoisomer of humulene epoxide II at a concentration of at least 0.1 and no greater than 1000 parts per million by weight.

14. The composition of claim 1, comprising either humulene epoxide III or a stereoisomer of humulene epoxide III at a concentration of at least 0.1 and no greater than 1000 parts per million by weight.

15. The composition of claim 1, comprising either humulenol or a stereoisomer of humulenol at a concentration of at least 0.1 and no greater than 1000 parts per million by weight.

* * * * *